United States Patent

Khambay et al.

[11] Patent Number: 5,880,162
[45] Date of Patent: Mar. 9, 1999

[54] PESTICIDAL FLUOROOLEFINS

[75] Inventors: Bhupinder Pall Singh Khambay, Southall; Mu-Guang Liu, Manchester, both of United Kingdom

[73] Assignee: British Technology Group, Ltd., London, England

[21] Appl. No.: 732,305

[22] PCT Filed: Apr. 26, 1995

[86] PCT No.: PCT/GB95/00954

§ 371 Date: Oct. 21, 1996

§ 102(e) Date: Oct. 21, 1996

[87] PCT Pub. No.: WO95/29887

PCT Pub. Date: Nov. 9, 1995

[30] Foreign Application Priority Data

Apr. 29, 1994 [GB] United Kingdom ............... 9408605

[51] Int. Cl.[6] ................... A01N 35/00; C07C 19/08; C07C 49/76

[52] U.S. Cl. .................... 514/683; 514/686; 514/687; 514/718; 514/719; 514/720; 570/128; 568/332; 568/333; 568/610

[58] Field of Search .................. 570/128; 568/332, 568/333, 610; 514/683, 686, 687, 718, 719, 720

[56] References Cited

U.S. PATENT DOCUMENTS 4,975,451 12/1990 Cullen et al. .

FOREIGN PATENT DOCUMENTS 2270693 3/1994 United Kingdom .
WO 85/04651 10/1985 WIPO .

Primary Examiner—Alan Siegel
Attorney, Agent, or Firm—Graham & James LLP

[57] ABSTRACT

A pesticidal compound of formula I:

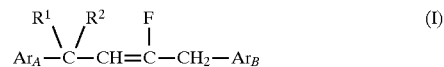

in which formula:

either $R^1$ is hydrogen and $R^2$ represents a cyclopropyl group or $R^1$ and $R^2$ each represent an alkyl group, which alkyl groups may be the same or different;

$Ar_A$ represents an optionally substituted phenyl or naphthyl group;

$Ar_B$ represents a phenoxy, phenyl, benzyl or benzoyl-substituted phenyl group which is optionally further substituted;

the configuration of the groups $Ar_A$—$CR^1R^2$ and —$CH_2Ar_B$ about the double bond being mutually trans.

Preferably $Ar_A$ is a substituted phenyl group; more preferably being substituted at the 4-(para) position by halogen, alkoxy or haloalkyl.

Further provided is a process for the preparation of a pesticidal compound of formula I in which a compound comprising a moiety

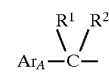

and a compound comprising a moiety $Ar_B$— are reacted together forming a link —CH═C(F)CH$_2$— between

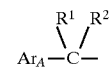

and $Ar_B$ in the compound of formula I.

12 Claims, No Drawings

PESTICIDAL FLUOROOLEFINS

This application is a 371 of PCT/GB95/00954 filed Apr. 26, 1995.

This invention relates to pesticidal non-ester pyrethroid olefins having a fluorine substituent at the site of olefinic unsaturation.

As there is evidence of the increased incidence of insect strains resistant to conventionally employed insecticides, so there is continuing interest in the development of new compounds with a new spectrum of activity against susceptible and also resistant species of insect.

Corresponding GB Patent Application No. 9219612.0 describes and claims certain arylcycloalkyl olefins having a fluoride substituent at the site of olefinic unsaturation, which arylcycloalkyl olefins exhibit useful activity as soil insecticides. It has now been found that certain novel 1-substituted, 1,4-diaryl-2-butenes having a 3-fluorine substituent, exhibit valuable activity against a range of insect pests.

Certain 1,4-diaryl-2-butenes have been reported as having insecticidal activity. Thus, U.S. Pat. No. 4,975,451 discloses certain cyclopropyl diaryl 2-butenes which exhibit insecticidal and acaricidal activity while Japanese Patent Publications Nos. 60115545, 60193902 and 60193940 report the existence of insecticidal activity in 1,1-dialkyl-1,4-diaryl 2-butenes. None of these documents discloses or suggests the introduction of a fluorine substituent at the site of olefinic unsaturation.

Therefore, according to the present invention there is provided a pesticidal compound of formula I:

$$Ar_A-\overset{R^1}{\underset{}{C}}\overset{R^2}{\underset{}{}}-CH=\overset{F}{\underset{}{C}}-CH_2-Ar_B \quad (I)$$

in which formula:
either $R^1$ is hydrogen and $R^2$ represents a cyclopropyl group or $R^1$ and $R^2$ each represent an alkyl group, which alkyl groups may be the same or different;

$Ar_A$ represents an optionally substituted phenyl or naphthyl group;

$Ar_B$ represents a phenoxy, phenyl, benzyl or benzoyl-substituted phenyl group which is optionally further substituted;

the configuration of the groups $Ar_A$—$CR^1R^2$ and —$CH_2Ar_B$ about the double bond being mutually trans.

Preferably $Ar_A$ is a substituted phenyl group. Substitution is preferably at the 4-(para) position, for example by halogen, alkoxy or haloalkoxy.

$Ar_B$ may be a phenyl group substituted by phenoxy, phenyl, benzyl or benzoyl, especially at the 3-(meta) position. Additionally the phenyl group may be substituted, especially by fluorine, especially at the 4-(para) position. 3-phenoxyphenyl and 4-fluoro-3-phenoxyphenyl groups are of particular interest.

One group of compounds in accordance with the invention are those represented by formula I where $R^1$ is hydrogen and $R^2$ represents a cyclopropyl group. A second group of compounds are represented by formula I where $R^1$ and $R^2$ each independently represent an alkyl group. Preferably $R^1$ and $R^2$ are both methyl.

The invention further includes a process for the preparation of a pesticidal compound of formula I in which a compound comprising a moiety $$Ar_A-\overset{R^1}{\underset{}{C}}\overset{R^2}{\underset{}{}}-$$

and a compound comprising a moiety $Ar_B$— are reacted together forming a link —CH=C(F)CH$_2$— between $$Ar_A-\overset{R^1}{\underset{}{C}}\overset{R^2}{\underset{}{}}-$$

and $Ar_B$ in the compound of formula I.

A preferred process comprises the catalytic reaction of a nucleophilic species formally of formula $Ar_B$— with a compound of formula $$Ar_A-\overset{R^1}{\underset{}{C}}\overset{R^2}{\underset{}{}}-CH=C(F)CH_2Q$$

where Q represents a good leaving group.

Typically, the reaction is carried out in the presence of a transition metal catalyst, which is preferably a copper salt or a complex thereof with a lithium salt.

The nucleophilic species $Ar_B$— is generally present in the form of a Grignard reagent of formula $Ar_B$MgBr or an alkali-metal compound, e.g. $Ar_B$Li, and the leaving group Q is typically halogen, e.g. bromine, or acyloxy, e.g. acetoxy. The copper salt is suitably a cuprous salt, especially a halide (e.g. bromide or iodide) or cyanide. Complexes of copper of formula Li$_2$ Cu Y$_2$Z$_2$ where Y and Z represent chlorine, bromine, iodine or cyano, may also be used as catalysts. Such transformations are described by Erdick, Tetrahedron, 1984, 40, 641–657.

The following route illustrates a typical procedure for preparation of compounds I where Q in the final step is acetoxy.

$$Ar_A\text{—CHO with }\overset{R^1}{\underset{}{C}}\overset{R^2}{\underset{}{}} \xrightarrow{Zn, CuCl, Ac_2O}_{Cl_2FC.CO_2Me} Ar_A-CH(CR^1R^2)-C(F)=CO_2Me$$

$$\xrightarrow{LiAlH_4} Ar_A-CH(CR^1R^2)-C(F)=CH_2OH$$

$$\xrightarrow{AcCl} Ar_A-CH(CR^1R^2)-C(F)=CH_2OAc$$

$$+ Ar_BMgBr \text{ or } Ar_BLi \xrightarrow{Cu\text{ halide or CuCN or Li}_2CuCl_4} I$$

The Grignard reagents $Ar_B$MgBr may be prepared by the methods and via the intermediates described in UK Patent Nos. 2226315 and 2187731 if desired.

The compounds of formula I can be used to combat pest infestation in the domestic, horticultural, agricultural or medical, (including veterinary) areas. The invention therefore also includes pesticidal compositions comprising a compound of formula I as an active ingredient together with an inert carrier or diluent.

Suitable diluents include both solid and liquid diluents so as to provide compositions which can be formulated for example as granules, dusts or emulsifiable concentrates. Examples of diluents suitable for the preparation of granular compositions are porous materials such as pumice, gypsum or corn cob grits. Suitable diluents for the preparation of dusts include kaolin, bentonite, kieselguhr or talc. For the preparation of emulsifiable concentrates, various solvents, such as ketones and aromatic solvents, may be employed together with one or more known wetting agents, dispersing agents or emulsifying agents.

Solid compositions especially granules, preferably contain from 0.5 to 15% by weight of active ingredient, while liquid compositions, as applied to the crop, may contain as little as from 0.0001 to 1% by weight of active ingredient. A composition such as a wettable powder however may contain as much as 75% by weight of active ingredient.

The compounds of formula I find particular application as soil insecticides, either for soil application or as a seed treatment although other uses are contemplated dependent on the pest to be combated and the focus of infestation.

Dependent on the mode of use, the compositions may conveniently be applied to the locus of infestation at an application rate of from 1 to 500 g of active ingredient per hectare.

It will be appreciated that the compositions may include a mixture of compounds of formula I and/or other ingredients, including another pesticidal material, eg. an insecticide, acaricide or fungicide, or a synergist.

The compositions may be used for combating soil borne pests such as those of the orders Coleoptera, Lepidoptera and Diptera, particularly root worms, cut worms, wireworms, millipedes, and wheat bulb fly. It is intended that the compositions may be applicable to soil and/or seeds during cultivation of a wide variety of crops such as maize, sugar beet, potatoes, tobacco and cotton.

The compounds of the invention have also been found to exhibit activity in combating such pests as houseflies, mustard beetles and diamondback moths.

The invention will now be further described with reference to the following examples.

Examples 1 to 15 relate to the preparation of intermediates, Examples 16 to 25 to the preparation of compounds of formula I and Example 26 to the use of compounds of the invention as insecticides. In the Examples 16 to 25, $^{13}$NMR peaks are listed as assigned peaks in the order indicated by the following diagrams:

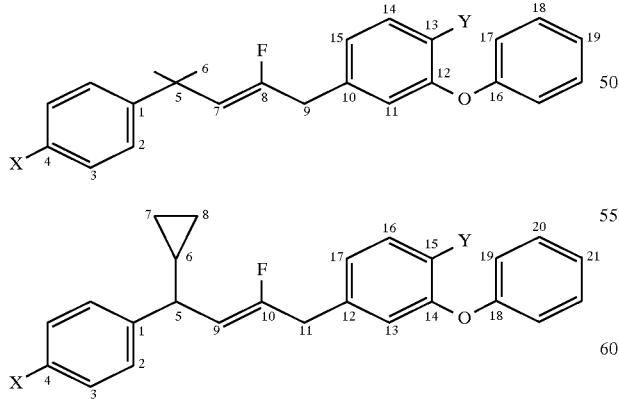

Equivocal assignments are indicated by superscripts, a,b. Peaks not detected above the noise level are indicated by N. Coupling constants to fluorine are given in brackets, and are in Hz.

EXAMPLE 1

Methyl 4-(4-Chlorophenyl)-4-cyclopropyl-2-fluorobut-2-enoate

To a stirred mixture of acid-washed zinc powder (0.88 g), copper (I) chloride (0.14 g) and molecular sieve 4A (2.0 g) in dry tetrahydrofuran (15 ml) under nitrogen, 1-(4-chlorophenyl)-1-cyclopropylacetaldehyde (1.07 g) (M. Elliott et al., Pestic. Sci., 1980, 11, 513–525) was added slowly, followed by acetic anhydride (0.47 ml). After the mixture had been warmed to 50°, methyl dichlorofluoroacetate (0.80 g) was added dropwise, and stirring continued for 4 hours at 50°. After cooling, the mixture was diluted with diethyl ether (150 ml), filtered through a bed of celite, and the filtrate was concentrated under reduced pressure. The residual oil was chromatographed on silica gel using diethyl ether/hexane (1:9) to yield ethyl 4-(4-chlorophenyl)4-cyclopropyl-2-fluorobut-2-enoate (0.92 g, 64%).

EXAMPLE 2

Methyl 4-cyclopropyl4-(4-ethoxyphenyl)-2-fluorobut-2-enoate

The method of Example 1 was repeated using zinc powder (4.0 g), copper (I) chloride (0.40 g), molecular sieve 4A (3.2 g), tetrahydrofuran (40 ml), 1-cyclopropyl (4-ethoxyphenyl) acetaldehyde (3.08 g) made from cyclopropyl (4-ethoxyphenyl) methanone by the method described by M. Elliott et al., Pestic. Sci., 1980.11, 513–525), acetic anhydride (1.4 ml) and methyl dichlorofluoroacetate (3.3 g) to yield the title compound (1.6 g, 39%).

EXAMPLE 3

Methyl 4-(4-chlorophenyl)-2-fluoro-4-methylpent-2-enoate

The method of Example 1 was repeated using zinc powder (1.86 g), copper (I) chloride (0.28 g) and molecular sieve 4A (2 g), tetrahydrofuran (30 ml), 2-(4-chlorophenyl)-2-methyl propionaldehyde (1.74 g (A. E. Baydar et al., Pestic. Sci. 1988, 23, 231–246). acetic anhydride (1.1 ml) and methyl dichlorofluoroacetate (1.6 g) to yield the title compound (1.4 g, 20%).

EXAMPLE 4

Methyl 4-(4-ethoxyphenyl)-2-fluoro-4-methylpent-2-enoate

The method of Example 1 was repeated using zinc powder (4 g), copper (I) chloride (0.58 g) and molecular sieve 4A (4.4 g), tetrahydrofuran (40 ml), 2-(4-ethoxyphenyl)-2-methylpropionaldehyde (3.6 g)(A. E. Baydar et al. Pestic. Sci., 1988, 23 247–257), acetic anhydride (2.1 ml) and methyl dichlorofluoroacetate (3.5 g) to yield the title compound (1.22 g, 22%).

EXAMPLE 5

Methyl 2-fluoro4-methyl-4-(4-trifluoromethoxyphenyl)pent-2-enoate

The method of Example 1 was repeated using zinc powder (3.4 g), copper (I) chloride (0.5 g), molecular sieve 4A (4 g), tetrahydrofuran (40 ml), 2-methyl-2-(4-trifluoromethoxyphenyl) propionaldehyde (2.2 g) (A. W. Farnham et al., Pestic. Sci. 1990, 28, 25–34), acetic anhydride (1.4 ml) and methyl dichlorofluoroacetate (2.9 g) to yield the title compound (0.49 g, 16%).

EXAMPLE 6

4-(4-Chlorophenyl)-4-cyclopropyl-2-fluorobut-2-enol

Methyl 4-(4-chlorophenyl)-4-cyclopropyl-2-fluorobut-2-enoate prepared as described in Example 1 (0.91 g) in dry diethyl ether (20 ml) was added dropwise to a stirred suspension of lithium aluminium hydride (0.34 g) in dry diethyl ether (25 ml) at 0° C. Stirring was continued during 40 minutes, while the mixture warmed to room temperature. Water (4 ml) was added, and the mixture was extracted with diethyl ether (3×20 ml). The combined organic layers were washed with water (3×10 ml), dried and evaporated under reduced pressure. The residual oil was chromatographed on silica gel using diethyl ether/hexane (2:3) to yield 4-(4-chlorophenyl)-4-cyclopropyl-2-fluorobut-2-enol (0.61 g, 78%).

EXAMPLE 7

4-cyclopropyl-4-(4-ethoxyphenyl)-2-fluorobut-2-enol

The method of Example 6 was repeated using methyl 4-cyclopropyl-4-(4-ethoxyphenyl)-2-fluorobut-2-enoate (Example 2) (1.2 g), diethyl ether (40 ml) and lithium aluminium hydride (0.2 g) to yield the title compound (1.05 g, 99%).

EXAMPLE 8

4-(4-Chlorophenyl)-2-fluoro-4-methylpent-2-enol

The method of Example 6 was repeated using methyl 4-(4-chlorophenyl)-2-fluoro-4-methylpent-2-enoate (Example 3) (0.56 g), diethyl ether (20 ml) and lithium aluminium hydride (0.21 g) to yield the title compound (0.35 g, 92%).

EXAMPLE 9

4-(4-Ethoxyphenyl)-2-fluoro-4-methylpent-2-enol

The method of Example 6 was repeated using methyl 2-fluoro-4-(4-ethoxy-phenyl)-4-methylpent-2-enoate (Example 4) (0.2 g), diethyl ether (15 ml) and lithium hydride (0.1 g) to yield the title compound (0.16 g, 90%).

EXAMPLE 10

2-fluoro-4-methyl4-(4-trifluoromethoxyphenyl)pent-2-enol

The method of Example 6 was repeated using methyl 2-fluoro-4-methyl-4-(4-trifluoromethoxyphenyl)pent-2-enoate (Example 5) (0.19 g), diethyl ether (10 ml) and lithium aluminium hydride (90 mg) to yield the title compound (0.16 g, 93%).

EXAMPLE 11

4-(4-Chlorophenyl)-4-cyclopropyl-2-fluorobut-2-enyl acetate

Acetyl chloride (1.2 ml) was slowly added to a stirred solution of 4-(4-chlorophenyl)-4-cyclopropyl-2-fluorobut-2-enol (Example 6) (0.51 g) in benzene (30 ml) and pyridine (0.24 ml) at 0° C. and stirring was continued for 24 hours while the mixture warmed to room temperature. Water (2 ml) was added, and the mixture was extracted with diethyl ether (3×20 ml). The combined organic layers were washed with water (3×10 ml), dried and evaporated under reduced pressure. The residual oil was chromatographed on silica gel using diethyl ether/hexane (1:4) to yield 4-(4-chlorophenyl)-4-cyclopropyl-2-fluorobut-2-enyl acetate (0.46 g, 78%).

EXAMPLE 12

4-Cyclopropyl-4-(4-ethoxyphenyl)-2-fluorobut-2-enyl acetate

The method of Example 11 was repeated using acetyl chloride (1.2 ml), 4-cyclopropyl-4-(4-ethoxyphenyl)-2-fluorobut-2-enol (Example 7) (0.65 g), benzene (34 ml) and pyridine (0.24 ml) to yield the title compound (0.75 g, 99%).

EXAMPLE 13

4-(4-Chlorophenyl)-2-fluoro-4-methylpent-2-enyl acetate

The method of Example 11 was repeated using acetyl chloride (0.76 ml), 4-(4-chlorophenyl)-2-fluoro4-methylpent-2-enol (Example 8) (0.34 g), benzene (20 ml) and pyridine (0.15 ml) to yield the title compound (0.35 g, 87%).

EXAMPLE 14

4-(4-Ethoxyphenyl)-2-fluoro-4-methylpent-2-enyl acetate

The method of Example 11 was repeated using acetate chloride (0.17 ml), 4-(4-ethoxyphenyl)-2-fluoro-4-methylpent-2-enol (Example 9) (86 mg), benzene (4 ml) and pyridine (0.04 ml) to yield the title compound (0.1 g, 99%).

EXAMPLE 15

2-Fluoro-4-methyl-4-(4-trifluoromethoxyphenyl)pent-2-enyl acetate

The method of Example 11 was repeated using acetyl chloride (0.41 ml), 2-fluoro-4-methyl-4-(4-trifluoromethoxyphenyl)pent-2-enol (Example 10) (0.2 g), benzene (10 ml) and pyridine (0.081 ml) to yield the title compound (0.23 g, 99%).

EXAMPLE 16

1-(4-chlorophenyl)-3-fluoro-4-(3-phenoxyphenyl) but-2-enyl) cyclopropane

A Grignard reagent was prepared from 3-phenoxyphenyl bromide (0.3 g) in dry tetrahydrofuran (2 ml) and magnesium (21 mg) under nitrogen using iodine as an initiator at ca 40° C. for 10 minutes. After cooling to −78° C., a solution of 4-(4-chlorophenyl)-4-cyclopropyl-2-fluorobut-2-enyl acetate (Example 11) (0.11 g) in tetrahydrofuran (1 ml) was added slowly with stirring, then the mixture was allowed to warm to room temperature overnight. Water (2 ml) was added and the mixture was extracted with diethyl ether (3×10 ml). The combined organic layers were washed with water (3×5 ml), dried, and evaporated under reduced pressure. The residual oil was purified by preparative thin layer chromatography (solvent: diethyl ether/hexane; 1:9) and then preparative high performance liquid chromatography (column: C 18; solvent: methanol; flow rate: 8 ml/min) to afford 1-(4-chlorophenyl)-3-fluoro-4-(3-phenoxyphenyl) but-2-enyl)cyclopropane (49.5 mg, 33%).

$^{13}$C NMR spectrum: 142.9, 128.4$^a$, 128.7$^a$, 131.0, 43.6 (4), 16.6, 3.8, 4.5, 110.0(15), N, 38.4(29), 138.3, 1 17.3, 157.5$^b$, 119.1, 129.8, 123.6, N$^b$, 118.9, 129.8, 123.3

EXAMPLE 17

1-(4-Ethoxyphenyl)-3-fluoro-4-(3-phenoxyphenyl) but-2-enyl) cyclopropane

The method of Example 16 was repeated using a Grignard reagent, prepared from 3-phenoxyphenyl bromide (0.53 g), tetrahydrofuran (4 ml) and magnesium (38 g), and 4-cyclopropyl-4-(4-ethoxyphenyl)-2-fluorobut-2-enyl acetate (Example 12) (0.18 g). The residue after evaporation was purified by preparative thin layer chromatography (solvent: diethyl ether/hexane (1:9) to afford 1-(4-ethoxyphenyl)-3-fluoro-4-(3-phenoxyphenyl)-but-2-enyl) cyclopropane (66.3 g, 28%).

$^{13}$C NMR spectrum: 136.3, 128.2, 114.3, $_{157.1}{}^a$, 43.2(4), 16.8, 3.7, 4.5, 110.6(15), 156.9(256), 38.8(30), 138.6, 117.2, 157.3$^a$, 119.1, 129.8, 123.6, 157.4$^b$, 118.9, 129.7, 123.2 and 63.4, 14.9 (OEt)

EXAMPLE 18

4-(4-Chlorophenyl)-2-fluoro-4-methyl-1-(3-phenoxyphenyl)pent-2-ene

The method of Example 16 was repeated using a Grignard reagent, prepared from 3-phenoxyphenyl bromide (0.19 g), tetrahydrofuran (2 ml) and magnesium (22 g), and 4-(4-chlorophenyl)-2-fluoro-4-methylpent-2-enyl acetate (Example 13) (0.12 g). The residue after evaporation was purified by preparative thin layer chromatography (solvent: diethyl ether/hexane; 1:9) and then preparative high performance liquid chromatography (column: C18; solvent: methanol; flow rate: 3 ml/min; to give the title compound (38 mg, 22%).

$^{13}$C NMR spectrum:
131.4, 128.1$^a$, 127.1$^a$, 148.4,38.5,30.1(3), 116.0(9), N, 39.1(29), 138.6, 117.2, 157.4$^b$, 119.0, 129.7, 123.6, 157.0$^b$, 118.9, 129.8, 123.3

EXAMPLE 19

4-(4-Ethoxyphenyl)-2-fluoro-4-methyl-1-(3-phenoxyphenyl)pent-2-ene

The method of Example 16 was repeated using a Grignard reagent, prepared from 3-phenoxyphenyl bromide (0.31 g), tetrahydrofuran (2 ml) and magnesium (24 mg), and 4-(4-ethoxyphenyl)-2-fluoro-methylpent-2-enyl acetate (Example 14) (70 mg). The residue after evaporation was purified by preparative thin layer chromatography (solvent: diethyl ether/hexane; 1:9) to give the title compound (44 mg, 45%/).

$^{13}$C NMR spectrum:
142.0, 126.6, 113.9, 157.1$^a$, 38.3, 30.2(3), 116.6(9), 156.7 (260), 39.2(29), 138.9,11, 117.1, 157.4$^b$, 119.1, 129.7, 123.6, 157.1$^a$, 118.9, 129.7, 123.3 and 63.3, 14.9 (OEt).

EXAMPLE 20

2-Fluoro-4-methyl-1-(3-phenoxyphenyl)-4-(4-trifluoromethoxyphenyl)pent-2-ene

The method of Example 16 was repeated using a Grignard reagent, prepared from 3-phenoxyphenyl bromide (0.3 g), tetrahydrofuran (2 ml) and magnesium (22 mg), and 2-fluoro4-methyl-4-(4-trifluoromethoxyphenyl)pent-2-enyl acetate (Example 15) (0.1 g). The residue after evaporation was purified by preparative thin layer chromatography (solvent: diethyl ether/hexane; 1:9) to give the title compound (56 mg, 42%).

$^{13}$C NMR spectrum:
148.6, 127.0, 120.4, 157.7$^a$, 38.6, 30.2(3), 115.9(10), 157.3(261),39.1(29), 138.6, 117.2, 157.5$^b$, 119.0, 129.8, 123.6, 151.1$^a$, 118.9, 129.8, 123.3.

EXAMPLE 21

1-(4-chlorophenyl)-3-fluoro-4-(4-fluoro-3-phenoxyphenyl)but-2-enyl)cyclopropane

The method of Example 16 was repeated using a Grignard reagent, prepared from 4-fluoro-3-phenoxyphenyl bromide (0.3 g), tetrahydrofuran (2 ml) and magnesium (21 mg), and 4-(4-chlorophenyl)-4-cyclopropyl-2-fluorobut-2-enyl acetate (Example 11) (0.14 g). The residue after evaporation was purified by preparative thin layer chromatography (solvent: diethyl ether/hexane; 1:9) and then preparative high performance liquid chromatography (column: C18; solvent: methanol; flow rate: 3 ml/min: to give the title compound (43 mg, 21%).

$^{13}$C NMR spectrum: 131.9, 128.5$^a$, 128.7$^a$, 1428, 43.6(4), 16.5, 3.8 4.5, 110.0(15), N, 37.9(29), N, 121.9, N, N, 117.0(20), 124.8(6), N, 129.7, 117.4, 123.2.

EXAMPLE 22

1-(4-Ethoxyphenyl)-3-fluoro-4-(4-fluoro-3-phenoxyphenyl)but-2-enyl)cyclopropane

The method of Example 16 was repeated using a Grignard reagent, prepared from 4-fluoro-3-phenoxyphenyl bromide (0.52 g), tetrahydrofuran (4 ml) and magnesium (32 mg), and 4-cyclopropyl4-(4-ethoxyphenyl)-2-fluorobut-2-enyl acetate (Example 12) (0.2 g). The residue after evaporation was purified by preparative thin layer chromatography (solvent: diethyl ether/hexane; 1:9) to give the title compound (56 mg, 20%).

$^{13}$C NMR spectrum: 136.2, 128.2, 114.3, 157.2$^a$, 43.2(4), 16.7, 3.7 4.5, 110.8(14), 156.8(255), 37.8(30), 133.4(4), 122.0, 143.6(12), 153.2(248), 116.9(18), 124.8(7), 157.4$^a$, 117.3, 129.7, 123.2 and 63.4, 14.9(OEt).

EXAMPLE 23

4-(4-Chlorophenyl-2-fluoro-1-(4-fluoro-3-phenoxyphenyl)-4-methylpent-2-ene

The method of Example 16 was repeated using a Grignard reagent, prepared from 4-fluoro-3-phenoxyphenyl bromide (0.36 g), tetrahydrofuran (4 ml) and magnesium (26 mg), and 4-(4-chlorophenyl)-2-fluoro-4-methylpent-2-enyl acetate (Example 13) (0.1 g). The residue after evaporation was purified by preparative thin layer chromatography (solvent: diethyl ether/hexane; 1:9) to give the title compound (68 mg, 43%).

$^{13}$C NMR spectrum: 131.4, 127.0$^a$, 128.1$^a$, 148.3, 38.5, 30.1(4), 116.0(10), 156.5(261), 38.5(29), 133.4(4), 121.8, 143.6(12), 153.2(248), 117.0(18), 124.8(8), 157.2, 117.4, 129.7, 123.2.

EXAMPLE 24

4-(4-Ethoxyphenyl)-2-fluoro-1-(4-fluoro-3-phenoxyphenyl)-4-methylpent-2-ene

The method of Example 16 was repeated using a Grignard reagent, prepared from 4-fluoro-3-phenoxyphenyl bromide (0.28 g), tetrahydrofuran (2 ml) and magnesium (20 mg), and 4-(4-ethoxyphenyl)-2-fluoro-4-methylpent-2-enyl acetate (Example 14) (60 mg). The residue after evaporation was purified by preparative thin layer chromatography (solvent: diethyl ether/hexane; 1:9) and then preparative high performance liquid chromatography (column: C18: solvent: 5% water in methanol; flow rate: 3 ml/min) to give the title compound (18 mg, 20%).

$^{13}$C NMR spectrum: 141.9, 121.5, 113.9 156.9, 38.2, 30.2(4), 116.8(9), N, 38.3(29), N, 121.9, N, N, 116.9(18), 124.8(7), 157.2, 117.4, 129.7, 123.2.

EXAMPLE 25

2-Fluoro-1-(4-fluoro-3-phenoxyphenyl)-4-methyl-4-(4-trifluoromethoxyphenyl)pent-2-ene The method of Example 16 was repeated using a Grignard reagent, prepared from 4-fluoro-3-phenoxyphenyl bromide (0.4 g), tetrahydrofuran (4 ml) and magnesium (26 mg), and 2-fluoro4-methyl-4-(4-trifluoromethoxyphenyl)pent-2-enyl acetate (Example 15) (90 mg). The residue after evaporation was purified by preparative thin layer chromatography (solvent: diethyl ether/hexane; 1:9) to give the title compound (40 mg, 33%).

$^{13}$C NMR spectrum: 148.4, 127.0, 120.5, N, 38.6,30.2(3), 116.1(10), 157.1(260), 38.5(29), 133.4(4), 121.8, 143.7(12), 153.2(248), 117.0(18), 124.8(7), 157.2 117.4, 129.8, 123.3.

EXAMPLE 26

Bioassay

Pesticidal activity was assessed against houseflies, mustard beetles, diamondback moth and cornroot worm, using the following techniques:

Houseflies (*Musca domestica*)

Female flies are treated on the thorax with a one microliter drop of insecticide dissolved in acetone. Two replicates of 15 flies are used at each dose rate and 6 dose rates are used per compound under test. After treatment, the flies are maintained at a temperature of 20°±1° and kill is assessed 24 and 48 hours after treatment. $LD_{50}$ values are calculated in micrograms of insecticide per fly and relative toxicities are calculated from the inverse ratios of the $LD_{50}$ values (see Sawicki et al., Bulletin of the World Health Organisation, 35, 893, (1966) and Sawicki et al., Entomologia and Exp. Appli. 10 253 (1967).

Mustard Beetles (*Phaedon cochleariae Fab*)

Acetone solutions of the test compound are applied ventrally to adult mustard beetles using a micro drop applicator. The treated insects are maintained for 48 hours after which time kill is assessed. Two replicates of 20 mustard beetles are used at each does level and 5 dose levels are used for each compound.

$LD_{50}$ values and thence relative potencies are calculated as for houseflies.

Diamondback moth (*Plutella xylostella*)

Fifth instar larvae are treated with 0.5 μl drop of insecticide in acetone. Three replicates of 10 larvae are used at each dose rate and 5 dose rates are used per compound under test. After treatment, the larvae are maintained at ca 22°, and kill is assessed as failure to pupate 5 days later. $LD_{50}$ values and relative potencies are calculated as for houseflies.

For all these three insect species the relative potencies are calculated by comparison with 5-benzyl-3-furylmethyl(1R)-trans-chrysanthemate (Bioresmethrin) which is one of the more toxic chrysanthemate esters known to these species.

Relative potencies to Houseflies, Mustard Beetles and Diamondback moth (Bioresmethrin=100) are given under HF, MB and PX respectively in Table 1 below.

Cornroot worm (*Diabrotica balteata*)

Residual soil activity was assessed as follows:

A known quantity of test compound dissolved in 1.0 ml acetone was applied evenly to a standard amount (22 g) of a sandy soil with a 10% moisture content. After 1 hour, 10 larvae were introduced. The temperature was maintained at 20° C.±1° C. and mortality assessed after 48 hours. Two replicates of 10 larvae were used at each of 5 dose levels per compound. $LC_{50}$ values were calculated as concentration of insecticide in the standard amount of soil using probit analysis.

Topical soil activity was assessed by treating late instar larvae with 1 μl drops of the insecticide in methylethylketone. Three replicates of 10 larvae are used at each dose rate, and 5 dose rates are used per compound under test. Mortality is assessed after 48 hours at 20° C. $LD_{50}$ values and thence relative potencies are calculated as for houseflies.

The residual and topical results are given in Table 1 below:

TABLE 1

| Ex No | HF[a] | MB[a] | PX[a] | Diabrotica Top[b] | Res[c] |
|---|---|---|---|---|---|
| 16 | 48 | 23 | ~66 | .009 | .36 |
| 17 | 9.5 | 40 | 160 | .024 | 0.7 |
| 18 | 9.5 | 1.6 | ~12 | .0041 | .17 |
| 19 | 25 | 4.7 | 61 | .005 | .3 |
| 20 | 16 | 13 | 48 | .054 | NA |
| 21 | 29 | 90 | ~180 | .005 | .03 |
| 22 | ~60 | 160 | ~320 | .008 | .026 |
| 23 | 11 | 5.2 | 70 | .003 | .02 |
| 24 | 40 | 24 | 90 | .013 | NA |
| 25 | 13 | 29 | ~220 | .019 | .37 |

[a]potencies relative to bioresmethrin = 100
[b]$LD_{50}$ in μg per larva
[c]$LC_{50}$ as ppm in soil

We claim:
1. A pesticide compound of formula I:

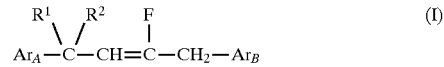

in which formula:
either $R^1$ is hydrogen and $R^2$ represents a cyclopropyl group or $R^1$ and $R^2$ each represent an alkyl group, which alkyl groups may be the same or different;

$Ar_A$ represents an optionally substituted phenyl or naphthyl group;

$Ar_B$ represents a phenoxy, phenyl, benzyl or benzoyl-substituted phenyl group which is optionally further substituted;

the configuration of the groups $Ar_A$—$CR^1R^2$ and —$CH_2Ar_B$ about the double bond being mutually trans.

2. A compound according to claim 1 wherein $Ar_A$ is a substituted phenyl group.

3. A compound according to claim 2 wherein the phenyl group is substituted at the 4-(para) position by halogen, alkoxy or haloalkyl.

4. A compound according to any one of claims 1 to 3 wherein $Ar_B$ is a phenyl group substituted at the 3-(meta) position by phenoxy, phenyl, benzyl or benzoyl.

5. A compound according to claim 4 wherein the phenyl group is further substituted by fluorine at the 4-(para) position.

6. A pesticidal composition comprising a pesticidally effective amount of a compound of formula I as defined in any one of claims 1 to 5 together with an acceptable carrier or diluent.

7. An insecticidal composition comprising a compound of formula I as defined in any one of claims 1 to 5 together with an inert carrier or diluent.

8. A composition according to claim 7 suitable for use in combating soil borne insect pests.

9. A composition according to any one of claims 6 to 8 in the form of granules, dust or emulsifiable concentrate.

10. A composition according to any one of claims 6 to 9 wherein the compound of formula I is present in an amount of from 0.5 to 5% by weight.

11. A method of combating soil borne insect pests comprising applying to the soil or as a seed treatment a composition according to any one of claims 7 to 10.

12. A method according to claim 11 wherein the rate of application is in the range of from 1 to 100 g active ingredient per hectare.

* * * * *